(12) United States Patent
Byun

(10) Patent No.: US 8,293,289 B2
(45) Date of Patent: Oct. 23, 2012

(54) PHARMACEUTICAL COMPOSITION FOR TREATMENT OF LUMBAR DISC HERNIATION AND PREPARATION METHOD THEREOF

(76) Inventor: Kyoung Sam Byun, Seoul (KR)

( * ) Notice: Subject to any disclaimer, the term of this patent is extended or adjusted under 35 U.S.C. 154(b) by 0 days.

(21) Appl. No.: 13/091,305

(22) Filed: Apr. 21, 2011

(65) Prior Publication Data

US 2011/0262568 A1 Oct. 27, 2011

(30) Foreign Application Priority Data

Apr. 23, 2010 (KR) ........................ 10-2010-0038152

(51) Int. Cl.
*A61K 36/00* (2006.01)
*A61K 36/254* (2006.01)
*A61K 36/286* (2006.01)
*A61K 36/489* (2006.01)
*A61K 36/296* (2006.01)
*A61K 36/8962* (2006.01)

(52) U.S. Cl. .......................... 424/725; 424/728; 424/754

(58) Field of Classification Search ........................ None
See application file for complete search history.

*Primary Examiner* — Qiuwen Mi
(74) *Attorney, Agent, or Firm* — Young & Thompson

(57) ABSTRACT

Disclosed are a pharmaceutical composition useful for treating lumbar disc herniation and a method for the preparation thereof. Composed of herbal ingredients, the pharmaceutical composition neither incurs resistance nor side effects, even when it is administered for a long term. The composition comprises *Acanthopanax senticosus* in an amount of 20~40 wt %, *Atractylodis Rhizoma Alba* in an amount of 30~50 wt %, *Carthamus tinctorius* seed powder in an amount of 3~10 wt %, *Sophora flavescens Aiton* in an amount of 5~15 wt %, *Achyranthis Bidentatae Radix* in an amount of 1~5 wt %, *Dipsaci Radix* in an amount of 1~5 wt %, pine knars in an amount of 1~5 wt %, *Epimedium Koreanum* in an amount of 1~5 wt %, and *Allium tuberosum* in an amount of 1~5 wt %.

1 Claim, No Drawings

PHARMACEUTICAL COMPOSITION FOR TREATMENT OF LUMBAR DISC HERNIATION AND PREPARATION METHOD THEREOF

BACKGROUND OF THE INVENTION

1. Field of the Invention

The present invention relates to a pharmaceutical composition for the treatment of lumbar disc herniations and a method for the preparation thereof. More particularly, the present invention relates to a pharmaceutical composition for the treatment of lumbar disc herniations which neither incurs resistance nor side effects, even when it is administered for a long term, and a method for preparing the same.

2. Description of the Related Art

A lumbar disc herniation is a medical condition affecting the spine, in which a tear in the outer, fibrous ring of an intervertebral disc allows the soft, central portion to bulge out, pressing against the spinal nerves, thus producing intense and usually disabling pain in the lumbar and legs. When intervertebral discs, which lie between adjacent vertebrae in the spine and act as shock absorbers to absorb the gravity and impact given to the body, are imparted with traumatic injury or when a person takes a wrong posture for a long period of time, the jelly-like content of the disc moves to the spinal canal, pressing the spinal nerve to cause pain and numbness. Lumbar disc herniations, also called "lumbar intervertebral disc herniation", occur in the lower back, most often between the fourth and fifth lumbar vertebral bodies or between the fifth and the sacrum in men in their thirties to fifties.

Typically, non-steroidal anti-inflammatory medications or muscle relaxants are tried for treating the pain of lumbar disc herniation, prior to surgery. However, this drug regimen can relieve the pain only, but cannot heal the disc herniation.

The long-term use of such drugs for patients with persistent back pain may cause drug resistance or side effects.

In addition, the symptoms of lumbar disc herniation can be improved by the drug regimen, but recur if the regimen is stopped.

SUMMARY OF THE INVENTION

Accordingly, the present invention has been made keeping in mind the above problems occurring in the prior art, and an object of the present invention is to provide a pharmaceutical composition for the treatment of lumbar disc herniations which can heal lumbar disc herniations as well as functioning as an analgesic, an antiphlogistic or a muscle relaxant, and a method for preparing the same.

Another object of the present invention is to provide a pharmaceutical composition for the treatment of lumbar disc herniations which neither incurs resistance nor side effects, even when it is administered for a long term, and a method for preparing the same.

A further object of the present invention is to provide a pharmaceutical composition for the treatment of lumbar disc herniations which can prevent the recurrence of lumbar disc herniations after they are healed, and a method for preparing the same.

The objects of the present invention could be accomplished by a provision of a composition for the treatment of lumbar disc herniations, comprising: *Acanthopanax senticosus* in an amount of 20~40 wt %, *Atractylodis Rhizoma Alba* in an amount of 30~50 wt %, *Carthamus tinctorius* seed powder in an amount of 3~10 wt %, *Sophora flavescens Aiton* in an amount of 5~15 wt %, *Achyranthis Bidentatae Radix* in an amount of 1~5 wt %, *Dipsaci Radix* in an amount of 1~5 wt %, pine knars in an amount of 1~5 wt %, *Epimedium Koreanum* in an amount of 1~5 wt %, and *Allium tuberosum* in an amount of 1~5 wt %.

Also, the present invention provides a method for preparing a pharmaceutical composition, comprising: a first step of producing a first dried powder by extracting 20~40 wt % of *Acanthopanax senticosus* and 30~50 wt % of *Atractylodis Rhizoma Alba* with hot water at 80~120° C. for 15~30 hours, concentrating the extract and drying the concentrate; a second step of producing a second dried powder by 3~10 wt % of *Carthamus tinctorius* seed powder, 5~15 wt % of *Sophora flavescens Aiton*, 1~5 wt % of *Achyranthis Bidentatae Radix*, 1~5 wt % of *Dipsaci Radix*, 1~5 wt % of pine knars, 1~5 wt % of *Epimedium Koreanum*, and 1~5 wt % of *Allium tuberosum* with hot water at 80~120° C. for 15~30 hours, concentrating the extract and drying the concentrate; and a third step of mixing the first dried powder and the second dried powder.

As described above, the pharmaceutical composition for the treatment of lumbar disc herniations in accordance with the present invention can heal lumbar disc herniations in addition to serving as an analgesic or antiphlogistic.

In addition, the pharmaceutical composition for the treatment of lumbar disc herniations in accordance with the present invention neither incurs resistance nor side effects, even when it is administered for a long term.

Further, the pharmaceutical composition for the treatment of lumbar disc herniations in accordance with the present invention can strengthen the bones, muscles and ligaments around the herniated disc, thus preventing the recurrence of the disc herniations after the herniated disc is healed.

Also, the method for the preparation of the pharmaceutical composition ensures effective extraction of ingredients necessary for the treatment of herniated disc.

DESCRIPTION OF THE PREFERRED EMBODIMENTS

Below, a detailed description will be given of the present invention.

In accordance with an aspect thereof, the present invention provides a composition for the treatment of lumbar disc herniations, comprising: *Acanthopanax senticosus* in an amount of 20~40 wt %, *Atractylodis Rhizoma Alba* in an amount of 30~50 wt %, *Carthamus tinctorius* seed powder in an amount of 3~10 wt %, *Sophora flavescens Aiton* in an amount of 5~15 wt %, *Achyranthis Bidentatae Radix* in an amount of 1~5 wt %, *Dipsaci Radix* in an amount of 1~5 wt %, pine knars in an amount of 1~5 wt %, *Epimedium Koreanum* in an amount of 1~5 wt %, and *Allium tuberosum* in an amount of 1~5 wt %.

*Acanthopanax senticosus*, found to have the highest medicinal benefits among various araliaceous shrubs, contains medicinally effective ingredients including eleutheroside B, eleutheroside E, isofraxidin, sesamin, chlorogenic acid and dicaffeoylquinic acid. *Acanthopanax senticosus* possesses the medicinal properties of suppressing the generation of lipid peroxide, a cause of cancer or aging, and hepatic functions and liver function metabolisms. Vasodilation, anti-hypertension, anti-cancer activity, anti-bacterial activity, anti-convulsive activity and anti-oxidative activity are also among the medicinal effects of *Acanthopanax senticosus*.

In accordance with the present invention, the pharmaceutical composition comprises *Acanthopanax senticosus* in an amount of from 20 to 40 wt % and preferably in an amount of 30 wt %. If the content of *Acanthopanax senticosus* is below wt %, the composition cannot effectively generate lipid peroxide. On the other hand, a content exceeding 40 wt % decreases the anti-hypertensive activity.

*Atractylodis Rhizoma Alba* is the root of *Atractylodes japonica* Koidzumi which is medicinally useful. In herbal medicine, *Atractylodis Rhizoma Alba* is prescribed to those whose spleen and stomach do not actively function; that is, those who lose appetite, feel tired, look pale and/or have diarrhea. In addition, taken routinely, *Atractylodis Rhizoma Alba* helps excrete water from the bodies of persons who become dropsical and suffer from indigestion due to water stagnation. Experiments with mice showed that *Atractylodis Rhizoma Alba* increased body weight and staying power and enhanced phagocytosis and cellular immunity. Further, the root was reported to have a suppressant action on the intestine, stimulation regulating activity, anti-ulcerative activity, hepatoprotective activity, immunopotentiating activity, vasodilative activity, diuretic activity, hypoglycemic activity, and anti-cancer activity.

In accordance with the present invention, *Atractylodis Rhizoma Alba* is used in an amount of from 30 to 50 wt %, and preferably in an amount of 40 wt %. If the content of *Atractylodis Rhizoma Alba* is below 30 wt %, the composition cannot enhance cellular immunity. On the other hand, a content exceeding 50 wt % allows water to be excessively excreted from the body, causing oligohydria.

*Carthamus tinctorius*, generically called safflower, is prescribed for female disorders, dysmenorrhea, and abdominal pain. Oil from its fruits may be used as a fuel or may be edible. Oil from its seeds is rich in linolic acid, thus being useful for the prevention and treatment of cholesterol-induced arteriosclerosis. In the present invention, a powder of *Carthamus tinctorius* seeds is used.

In accordance with the present invention, the composition contains a powder of *Carthamus tinctorius* seeds in an amount of from 3 to 10 wt %, and preferably in an amount of 5 wt %. If the content of the powder of *Carthamus tinctorius* seeds is less than 3 wt %, there are no effects of reducing blood cholesterol levels. On the other hand, if the content exceeds 10 wt %, the composition may cause slight abdominal pain.

*Sophora flavescens Aiton*, belonging to the genus *Sophora*, is a perennial shrub growing in the wild in Northeast Asia and it tastes bitter. In herbal medicine, this plant is used for the treatment of leukopenia, and is also reported to show anti-radiation activity, anti-cancer activity, anti-bacterial activity and immunopotentiating activity and to have the activity of increasing coronary flow, strengthening the heart muscles, and reducing blood glucose levels.

In accordance with the present invention, the composition contains *Sophora flavescens Aiton* in an amount of from 5 to 15 wt % and preferably in an amount of 10 wt %. When *Sophora flavescens Aiton* is used in an amount less than 5 wt %, the composition cannot contribute to increasing immunity. On the other hand, a content exceeding 15 wt % may cause an excessive reduction in blood glucose level.

The *Achyranthis Bidentatae Radix* used in the present invention is a dried root of *Achyranthes Japonica Nakai*. In the roots, olenolic saponins, steroidal inokosterone and ecdysterone are found. In herbal medicine, the roots are prescribed for hypertension, rheumatoid arthritis, and congestion or as a diuretic agent or a tonic agent. *Achyranthis Bidentatae Radix* was also known to show anti-inflammatory activity, anti-oxidative activity, hepatoprotective activity, anti-allergic activity and anti-cancer activity.

The composition of the present invention contains *Achyranthis Bidentatae Radix* in an amount of from 1 to 5 wt %, and preferably in an amount of 3 wt %. If *Achyranthis Bidentatae Radix* is used in an amount less than 1 wt %, the composition cannot exhibit sufficient anti-inflammatory activity and anti-oxidative activity. On the other hand, when the content of the root is over 5 wt %, the composition may deteriorate liver function.

*Dipsaci Radix* is a medicine made of the roots of *Dipsacus asperoides* belonging to the family Dipsacaceae and contains sucrose, daucosterol, β-stegmasterol, triterpenoidal saponin, hederagenin, ursol aldehyde, and ursolic acid. In herbal medicine, *Dipsaci Radix* is known to protect the liver and the spleen and to promote blood circulation and is prescribed for pain in the waist and the knee, arthritis, and fatigue-induced arthralgia. The root is reported to have the medicinal activity of increasing the number of leukocytes, stimulating the uterine and inhibiting the growth of *Diplococcus pneumonia*.

In the present invention, *Dipsaci Radix* is used in an amount of 1 to 5 wt % and preferably in an amount of 3 wt %. If the content of the root is less than 1 wt %, the composition cannot actively circulate blood. On the other hand, a content exceeding 5 wt % cannot reduce fatigue-induced arthralgia.

A pine knar is a portion of a pine tree from which a new branch starts to grow. The term "pine knar," as used herein, is intended to refer to a rosin-deposited knot on a pine tree. In herb medicine, pine knars are prescribed for ostalgia, beriberi, bruises and arthritis. They are also known to have beneficial medicinal effects on hair loss, poisoning, insomnia, heart disease, coughs, and digestive diseases.

In the present invention, pine knars are used in an amount of from 1 to 5 wt % and preferably in an amount of 3 wt %. If the composition contains pine knars in an amount less than 1 wt %, it cannot alleviate ostalgia. On the other hand, a content exceeding 5 wt % may cause insomnia.

In herb medicine, *Epimedium Koreanum* is applied to the treatment of impotence, spermatorrhea, uterine coldness, cold hypersensitivity of the hands and feet, facial palsy, amnesia, paralysis, unsoundness in the waist and knees, hypertension and infantile paralysis. In addition, *Epimedium koreanum* is known for its medicinal activities including the promotion of semen secretion, the reduction of blood pressure, the increase of coronary flow, the reduction of blood glucose level, reduction of blood cholesterol level, the potentiation of immunity, antibethic activity, the discharge of phlegm, tranquilization, and antiphlogistic activity.

In the present invention, *Epimedium koreanum* is used in an amount of from 1 to 5 wt % and preferably in an amount of 3 wt %. The composition with the content of *Epimedium koreanum* less than 1 wt % cannot ensure the tranquilizing and antiphlogistic activity. On the other hand, when the content of *Epimedium koreanum* is over 5 wt %, the composition shows a delayed hypotensive effect.

*Allium tuberosum* is known to enhance virility and is thus called a "virility enhancing plant." In addition to being a food material, *Allium tuberosum* has been used as a medicinal material in herbal medicine. The famous Chinese ancient medicinal literature *Bencao Gangmu* describes how *Allium tuberosum* warms the body and potentiates the function of the genitals." According to *Bencao Beiyao*, another famous Chinese medicinal literature, *Allium tuberosum* has the pharmaceutical activity of enhancing male virility, aiding the function of the lungs, and protecting the stomach. The plant is also said to promote blood circulation throughout the body, eliminate toxic materials from the intestines, potentiate immunity and bind the bowels.

In the present invention, *Allium tuberosum* is used in an amount of from 1 to 5 wt % and preferably in an amount of 3 wt %. If the content of *Allium tuberosum* is less than 1 wt %, the pharmaceutical composition cannot perform the function of circulating blood, well. On the other hand, a content exceeding 5 wt % promotes too much virility.

In accordance with another aspect thereof, the present invention pertains to a method for preparing the pharmaceutical composition for the treatment of lumbar disc herniation.

The method comprises a first step of producing a first dried powder by extracting 20~40 wt % of *Acanthopanax senticosus* and 30~50 wt % of *Atractylodis Rhizoma Alba* with hot water at 80~120° C. for 15~30 hours, concentrating the extract and dry the concentrate; a second step of producing a second dried powder by 3~10 wt % of *Carthamus tinctorius* seed powder, 5~15 wt % of *Sophora flavescens Aiton*, 1~5 wt % of *Achyranthis Bidentatae Radix*, 1~5 wt % of *Dipsaci Radix*, 1~5 wt % of pine knars, 1~5 wt % of *Epimedium Koreanum*, and 1~5 wt % of *Allium tuberosum* with hot water at 80~120° C. for 15~30 hours, concentrating the extract and drying the concentrate; and mixing the first dried powder and the second dried powder.

Alternatively, the herbs may be powdered or extracted individually. Individual extracts thus obtained may be mixed. In another alternative, necessary herbs may be mixed before extraction. A detailed procedure is given below.

After being immersed in water for 20~30 hours and preferably for 24 hour, *Acanthopanax senticosus* and *Atractylodis Rhizoma Alba* are boiled at 80~120° C. and preferably at 100° C. for 15~30 hours and preferably for 24 hours and filtered to give an extract. The extract was concentrated and dried to produce a first dried powder.

Separately, *Carthamus tinctorius* seed powder, *Sophora flavescens Aiton*, *Achyranthis Bidentatae Radix*, *Dipsaci Radix*, pine knars, *Epimedium Koreanum* and *Allium tuberosum* are immersed together in water and boiled at 80~120° C. and preferably at 100° C. for 15~30 hours and preferably for 24 hours, followed by filtration to give an extract. The extract was concentrated and dried to produce a second dried powder.

Next, the first dried powder and the second dried powder are mixed together to prepare a pharmaceutical composition for the treatment of lumbar disc herniation.

The mixed, herbal extract of the present invention is useful for treating lumbar disc herniation. The extract may be preferably formulated into an oral dosage form, such as capsules.

In accordance with the present invention, the pharmaceutical composition may be administered once a day at a daily dose of 2 mg~3 mg, preferably 30 min before sleep. More preferably, the body temperature is maintained at 36.5° C. during the intake of the composition. In this context, the patient may wear an abdominal bandage or may take the capsule together with warm water or tea.

A better understanding of the present invention may be obtained through the following examples which are set forth to illustrate, but are not to be construed as limiting the present invention.

EXAMPLE

In water, 600 g of *Acanthopanax senticosus* and 800 g of *Atractylodis Rhizoma Alba* were boiled at 100° C., followed by filtration. The filtrate was concentrated and dried to give 71 g of an extract.

Together with 120 g of *Carthamus tinctorius* seed powder, 180 g of *Sophora flavescens Aiton*, 60 g of *Achyranthis Bidentatae Radix*, 60 g of *Dipsaci Radix*, 60 g of pine knars, 60 g of *Epimedium Koreanum*, and 60 g of *Allium tuberosum* were boiled in water at 100° C. for 24 hours, followed by filtration. The filtrate was concentrated and dried to produce about 25 g of an extract.

The extracts were mixed for use as a pharmaceutical composition.

Experimental Example

Clinical Experiment

The composition prepared in the Example was formulated into an oral capsule and administered to a group of patients suffering from herniated disc (hereinafter referred to as "Group 1") and a group of patients suffering from lumbago or numbness (hereinafter referred to as "Group 2"). The patients were composed of 25 males and 25 females in their thirties to fifties.

The composition was administered once a day at a daily dose of 2 mg over three months, with a monthly survey taken of medicinal effects on disc herniation and pain.

The medicinal effects were scored according to a seven-point method in which one point was set for no effects, three points for somewhat effect, five points for good effects, and seven points for excellent effects. The results are summarized in Table 1, below.

TABLE 1

| Group | Disc Treatment | Pain Relief | Recurrence Rate |
|---|---|---|---|
| Group 1 | 5.0 | | 7/47 |
| Group 2 | | 5.68 | 5/46 |

When administered with the oral capsule of the present invention, as shown in Table 1, the herniated disc patients of Group 1 experienced positive medicinal effects. Also, the pain was relieved to a significant degree in the lumbago or numbness patients of Group 2.

One month after the administration of the composition was terminated, the patients were examined for the recurrence of the disc herniation, or lumbago, or numbness. Only seven suffered from lumbar disc herniation among 47 subjects of Group 1 who had experienced a medicinal effect. As for Group 2, only five suffered from lumbago or numbness among 46 subjects who had experienced a medicinal effect. Therefore, the pharmaceutical composition of the present invention showed a recurrence rate of about 10%.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A pharmaceutical composition for treatment of lumbar disc herniation, comprising *Acanthopanax senticosus* in an amount of 20~40 wt %, *Atractylodis Rhizoma Alba* in an amount of 30~50 wt %, *Carthamus tinctorius* seed powder in an amount of 3~10 wt %, *Sophora flavescens Aiton* in an amount of 5~15 wt %, *Achyranthis Bidentatae Radix* in an amount of 1~5 wt %, *Dipsaci Radix* in an amount of 1~5 wt %, pine knars in an amount of 1~5 wt %, *Epimedium Koreanum* in an amount of 1~5 wt %, and *Allium tuberosum* in an amount of 1~5 wt %.

* * * * *